US011360734B1

(12) United States Patent
Liu et al.

(10) Patent No.: US 11,360,734 B1
(45) Date of Patent: Jun. 14, 2022

(54) SECURE DIGITAL COMMUNICATION DEVICES AND SECURE DIGITAL COMMUNICATION SYSTEMS USING THE SAME

(71) Applicant: Shanghai Weiling Electronics Co., Ltd., Shanghai (CN)

(72) Inventors: Danqing Liu, Shanghai (CN); Shijian Liu, Shanghai (CN)

(73) Assignee: Shanghai Weiling Electronics Co., Ltd., Shanghai (CN)

( * ) Notice: Subject to any disclaimer, the term of this patent is extended or adjusted under 35 U.S.C. 154(b) by 0 days.

(21) Appl. No.: 17/483,983

(22) Filed: Sep. 24, 2021

(51) Int. Cl.
*G16H 30/20* (2018.01)
*G06F 3/16* (2006.01)
*G06F 21/60* (2013.01)

(52) U.S. Cl.
CPC .............. *G06F 3/162* (2013.01); *G06F 3/165* (2013.01); *G06F 21/606* (2013.01); *G16H 30/20* (2018.01)

(58) Field of Classification Search
CPC ..... A61B 5/369; A61B 17/3403; A61B 5/681; G06F 3/162; G06F 3/165; G06F 11/3684; G06F 16/16; G06F 16/40; G06F 16/5866; G06F 21/606; G06F 21/608; G06F 3/04897; G06N 3/08; G06N 5/04; G06Q 10/00; G06Q 10/10; G06T 15/205; G06V 10/82; G16H 15/00; G16H 30/20; G16H 40/20; G16H 40/67; G16H 50/20; G16H 20/10; H04L 9/3239; H04L 65/60; H04L 67/00; H04L 67/12; H04L 69/329; H04N 19/34; H04N 19/48; H04N 19/59; H04N 19/895; H04B 11/00; H04R 1/1041; H04R 3/005; H04W 4/80
USPC ................ 380/33; 382/128; 600/407; 705/2, 705/14.53; 707/661, 710, 770; 709/231, 709/217; 713/176, 193; 714/48; 726/26
See application file for complete search history.

(56) References Cited

U.S. PATENT DOCUMENTS 5,671,353 A * 9/1997 Tian ......................... H04L 67/00
714/48
6,557,102 B1 * 4/2003 Wong ..................... G06F 21/608
713/176
6,574,629 B1 * 6/2003 Cooke, Jr. ............... G06F 16/40
(Continued)

*Primary Examiner* — Gerald Gauthier
(74) *Attorney, Agent, or Firm* — Ming Jiang; MM IP Services LLC

(57) ABSTRACT

Aspects of present disclosure relates to a secure digital communication device. In certain embodiments, secure digital communication device (SDCD) includes: a streaming signal CODEC, and a streaming signal transceiver. SDCD is installed between intranet and internet over firewall to form a physical isolation of intranet and internet. When streaming signal CODEC of a first SDCD receives digital contents, streaming signal CODEC of the first SDCD encodes digital contents into streaming signal, transmits streaming signal to a streaming signal transceiver of the first SDCD, streaming signal transceiver of the first SDCD transmits streaming signal over internet to another streaming signal transceiver of second SDCD. The streaming signal transceiver of the second SDCD transmits streaming signal to a second streaming signal CODEC of the second SDCD, the streaming signal CODEC decodes the streaming signal to digital contents, and transmits digital contents out of secure digital communication device through streaming signal CODEC.

18 Claims, 13 Drawing Sheets

(56) References Cited

U.S. PATENT DOCUMENTS

| | | | | |
|---|---|---|---|---|
| 7,660,413 B2* | 2/2010 | Partovi | ................... | G06Q 10/10 |
| | | | | 705/3 |
| 9,536,324 B1* | 1/2017 | Fram | ................... | H04N 19/895 |
| 10,204,117 B2* | 2/2019 | Chau | ................... | G16H 30/20 |
| 11,094,416 B2* | 8/2021 | Fram | ................... | G16H 50/20 |
| 2005/0027995 A1* | 2/2005 | Menschik | ............. | G16H 40/67 |
| | | | | 713/193 |
| 2006/0058603 A1* | 3/2006 | Dave | ................... | A61B 5/369 |
| | | | | 600/407 |
| 2009/0262991 A1* | 10/2009 | Thiagarajan | ........... | H04N 19/59 |
| | | | | 382/233 |
| 2010/0114951 A1* | 5/2010 | Bauman | ................. | G16H 30/20 |
| | | | | 707/E17.031 |
| 2011/0282844 A1* | 11/2011 | Bates | ...................... | G06F 16/16 |
| | | | | 707/661 |
| 2012/0221346 A1* | 8/2012 | Acker | ................... | G06Q 10/00 |
| | | | | 705/2 |
| 2012/0250956 A1* | 10/2012 | Bocirnea | ................ | H04N 19/48 |
| | | | | 382/128 |
| 2013/0166767 A1* | 6/2013 | Olivier | ................... | H04L 65/60 |
| | | | | 709/231 |
| 2013/0268357 A1* | 10/2013 | Heath | ................... | G06Q 10/10 |
| | | | | 726/26 |
| 2014/0156630 A1* | 6/2014 | Yin | ...................... | G06F 11/3684 |
| | | | | 707/710 |
| 2014/0341450 A1* | 11/2014 | Sedan | ................... | H04N 19/34 |
| | | | | 382/128 |
| 2015/0113094 A1* | 4/2015 | Williams | ............... | H04B 11/00 |
| | | | | 709/217 |
| 2016/0365021 A1* | 12/2016 | Hancock | ............. | G06F 3/04897 |
| 2017/0109486 A1* | 4/2017 | Tran | ...................... | G16H 20/10 |
| 2017/0228692 A1* | 8/2017 | Pargoe | ................... | H04W 4/80 |
| 2017/0300358 A1* | 10/2017 | Rahme | ................... | G16H 15/00 |
| 2017/0325786 A1* | 11/2017 | Pepe | ...................... | G16H 40/20 |
| 2017/0337493 A1* | 11/2017 | Paramasivan | .......... | G16H 40/20 |
| 2018/0018444 A1* | 1/2018 | Rahme | ................... | H04L 67/12 |
| 2018/0103859 A1* | 4/2018 | Provenzano | ........... | A61B 5/681 |
| 2018/0373659 A1* | 12/2018 | Amarilio | ............... | H04R 3/005 |
| 2019/0065763 A1* | 2/2019 | Berg | ...................... | H04L 9/3239 |
| 2020/0281624 A1* | 9/2020 | Hetzel | ............... | A61B 17/3403 |
| 2020/0310751 A1* | 10/2020 | Anand | ................ | H04R 1/1041 |
| 2020/0327661 A1* | 10/2020 | Oved | ...................... | G06V 10/82 |
| 2020/0351586 A1* | 11/2020 | Fei | ........................ | H04R 3/005 |
| 2020/0379716 A1* | 12/2020 | Carrigan | .......... | H04N 21/42208 |
| 2020/0382872 A1* | 12/2020 | Carrigan | ................... | H04R 5/02 |
| 2021/0201190 A1* | 7/2021 | Edgar | ....................... | G06N 5/04 |
| 2021/0275918 A1* | 9/2021 | Devaranjan | ........... | G06T 15/205 |
| 2021/0406642 A1* | 12/2021 | Chorakhalikar | ......... | G06N 3/08 |
| 2021/0407671 A1* | 12/2021 | Asayonak | ........... | G06F 16/5866 |
| 2022/0116821 A1* | 4/2022 | Wei | ....................... | H04L 5/0094 |

\* cited by examiner

|        | 1209 HZ | 1336 HZ | 1477 HZ | 1633 HZ |
|--------|---------|---------|---------|---------|
| 697 HZ | 1       | 2       | 3       | A       |
| 770 HZ | 4       | 5       | 6       | B       |
| 852 HZ | 7       | 8       | 9       | C       |
| 941 HZ | *       | 0       | #       | D       |

DUAL-TONE MULTI-FREQUENCY (DTMF) SIGNALING

Electronic Application Form

APP No.: 7674881/82    Patient Rec. No.: 0023223661

Name: Wu, Wenguang | Gender: Male | Age: 95

Source: In-Patient | Outpatient No.: | In-Patient No.: 920267975

Phone No.: +86.136.3361.6476 | Address:

Examination Detail: Color Doppler ultrasonography of single lower limb blood vessels (including arteriovenous)

Examination Position: Color Doppler ultrasonography of single lower limb blood vessels (including arteriovenous)

Clinical diagnosis: acute cerebrovascular disease

Patient Complaint: Development: Normal; | Nutrition: Well
Facial Appearance: Normal | Expression: Normal
Posture: Natural | Examination: Cooperative Patient History: The patient developed weakness of the right limb nine hours before admission, mainly manifested as raising right upper limb but unable to Hold steady, dragging right lower limb when walking, and no dizziness, headache, nausea and vomiting during the course of the disease.

Specific Symptoms:

Department: Neurology | Doctor: Duan, Surong | Date: 2021-07-28

EXEMPLARY ULTRASONIC IMAGE

US 11,360,734 B1

SECURE DIGITAL COMMUNICATION DEVICES AND SECURE DIGITAL COMMUNICATION SYSTEMS USING THE SAME

FIELD

The present disclosure generally relates to internet communication, and more particularly to secure digital communication devices, and secure digital communication systems and secure Picture Archiving and Communication Systems using the secure digital communication devices.

BACKGROUND

PACS (picture archiving and communication system) is a medical imaging technology used primarily in healthcare organizations to securely store and digitally transmit electronic images and clinically-relevant reports. The use of PACS eliminates the need to manually file and store, retrieve and send sensitive information, films and reports. Instead, medical documentation and images can be securely housed in off-site servers and safely accessed essentially from anywhere in the world using PACS software, workstations and mobile devices.

Safety, security and patient privacy are of paramount importance when still images, videos, as well as patient reports are transmitted from computer workstations to PACS servers. In order to avoid MITM (Man-In-The-Middle) attacks, ARP (Address Resolution Protocol) poisoning and virus infections, certain security measures have to be implemented such that the documents such as reports from an intranet are transported over an open internet through physical isolation between the intranet and the internet without direct physical connections.

Therefore, heretofore unaddressed needs still exist in the art to address the aforementioned deficiencies and inadequacies.

SUMMARY

In one aspect, the present disclosure relates to a secure digital communication device. In certain embodiments, the secure digital communication device includes: a streaming signal CODEC and a streaming signal transceiver. The streaming signal CODEC includes a first interface and a second interface. The streaming signal transceiver includes a first interface and a second interface. In certain embodiments, the secure digital communication device is installed in a workstation between an intranet and an internet over a firewall to form a physical isolation of the intranet and the internet.

In certain embodiments, when a streaming signal CODEC of a first secure digital communication device of a first workstation receives a set of digital contents from the intranet through the first interface, the streaming signal CODEC of the first secure digital communication device encodes the set of digital contents received into a streaming signal, transmits the streaming signal through the second interface of the streaming signal CODEC of the streaming signal CODEC to a first interface of the streaming signal transceiver of the first secure digital communication device. The streaming signal transceiver of the first secure digital communication device transmits the streaming signal through the second interface to a second interface of a streaming signal transceiver of a second secure digital communication device of a second workstation over the internet, and when the streaming signal transceiver of the second secure digital communication device receives the streaming signal through the second interface over the internet, the streaming signal transceiver of the second secure digital communication device transmits the streaming signal through the first interface of the streaming signal transceiver of the second secure digital communication device to the second interface of the streaming signal CODEC of the second secure digital communication device, the streaming signal CODEC of the second secure digital communication device decodes the streaming signal to the set of digital contents, and stores the set of digital contents decoded in the second workstation.

In certain embodiments, the set of digital contents includes a word document, a spread sheet document, a power point presentation document, a PDF document, a text document, a still image, a video segment, and any combination thereof.

In certain embodiments, the streaming signal includes an audio handshake signal, and a streaming media signal. The audio handshake signal coordinates the transmission of the streaming media signal. The streaming media signal of the streaming signal includes one or more QR codes, one or more color images, and one or more video segments.

In certain embodiments, an HDMI interface is installed between the second interface of the streaming signal CODEC and the first interface of the streaming signal transceiver of the secure digital communication device. The streaming signal is transmitted over the HDMI interface. The audio handshake signal of the streaming signal is transmitted through an audio channel of the HDMI interface. The streaming media signal is transmitted through a display data channel of the HDMI interface.

In another aspect, the present disclosure relates to a secure digital communication system. In certain embodiments, the secure digital communication system includes: a secure digital communication system server, a group of workstations, and each workstation includes a secure digital communication device. The secure digital communication system server is connected to a database, and a server secure digital communication device. Each of the group of workstations is installed in an intranet, the workstations are connected to the secure digital communication system server over an internet. Each secure digital communication device connects a corresponding workstation to the server secure digital communication device of the secure digital communication system server to facilitate secure communication among the group of workstations and the secure digital communication system server.

In certain embodiments, each of secure digital communication devices and the server secure digital communication device includes: a streaming signal CODEC and a streaming signal transceiver. The streaming signal CODEC includes a first interface and a second interface. The streaming signal transceiver includes a first interface and a second interface. The secure digital communication device is installed in a workstation between the intranet and the internet over a firewall to form a physical isolation of the intranet and the internet.

In certain embodiments, when a streaming signal CODEC of a first secure digital communication device of a first workstation receives a set of digital contents from the intranet through the first interface, the streaming signal CODEC of the first secure digital communication device encodes the set of digital contents received into a streaming signal, transmits the streaming signal through the second interface of the streaming signal CODEC of the streaming signal CODEC to a first interface of the streaming signal transceiver of the first secure digital communication device. The streaming signal transceiver of the first secure digital communication device transmits the streaming signal through the second interface to a second interface of a streaming signal transceiver of a second secure digital communication device of a second workstation over the internet, and when the streaming signal transceiver of the second secure digital communication device receives the streaming signal through the second interface over the internet, the streaming signal transceiver of the second secure digital communication device transmits the streaming signal through the first interface of the streaming signal transceiver of the second secure digital communication device to the second interface of the streaming signal CODEC of the second secure digital communication device, the streaming signal CODEC of the second secure digital communication device decodes the streaming signal to the set of digital contents, and stores the set of digital contents decoded in the second workstation.

In certain embodiments, the set of digital contents includes a word document, a spread sheet document, a power point presentation document, a PDF document, a text document, a still image, a video segment, and any combination thereof.

In certain embodiments, the streaming signal includes an audio handshake signal, and a streaming media signal. The audio handshake signal coordinates the transmission of the streaming media signal. The streaming media signal of the streaming signal includes one or more QR codes, one or more color images, and one or more video segments.

In certain embodiments, an HDMI interface is installed between the second interface of the streaming signal CODEC and the first interface of the streaming signal transceiver of the secure digital communication device. The streaming signal is transmitted over the HDMI interface. The audio handshake signal of the streaming signal is transmitted through an audio channel of the HDMI interface. The streaming media signal of the streaming signal is transmitted through a display data channel of the HDMI interface.

In yet another aspect, the present disclosure relates to secure Picture Archiving and Communication System (PACS). In certain embodiments, the secure PACS 20 includes: a secure PACS server, a group of workstations, and each workstation includes a secure digital communication device. The secure PACS server is connected to a PACS database, and a server secure digital communication device. Each of the group of workstations is installed in an intranet, the workstations are connected to the secure PACS server over an internet. Each secure digital communication device connects a corresponding workstation to the server secure digital communication device of the secure PACS server to facilitate secure communication among the group of workstations and the secure PACS server.

In certain embodiments, each of secure digital communication devices and the server secure digital communication device includes: a streaming signal CODEC and a streaming signal transceiver. The streaming signal CODEC includes a first interface and a second interface. The streaming signal transceiver includes a first interface and a second interface. The secure digital communication device is installed in a workstation between the intranet and the internet over a firewall to form a physical isolation of the intranet and the internet.

In certain embodiments, when a streaming signal CODEC of a first secure digital communication device of a first PACS workstation receives a set of PACS contents from the intranet through the first interface, the streaming signal CODEC of the first secure digital communication device encodes the set of PACS contents received into a streaming signal, transmits the streaming signal through the second interface of the streaming signal CODEC to a first interface of a streaming signal transceiver of the first secure digital communication device, the streaming signal transceiver of the first secure digital communication device transmits the streaming signal through the second interface to a second interface of a streaming signal transceiver of a second secure digital communication device of a second PACS workstation over the internet. When the streaming signal transceiver of the second secure digital communication device receives the streaming signal through the second interface of the second secure digital communication device over the internet, the streaming signal transceiver of the second secure digital communication device transmits the streaming signal through the first interface of the streaming signal transceiver of the second secure digital communication device to the second interface of a streaming signal CODEC of the second secure digital communication device, the streaming signal CODEC of the second of the second secure digital communication device decodes the streaming signal to the set of PACS contents, and stores the set of PACS contents decoded in the second PACS workstation.

In certain embodiments, the set of PACS contents includes a word document, a spread sheet document, a power point presentation document, a PDF document, a text document, a still image, a video segment, and any combination thereof.

In certain embodiments, the streaming signal includes an audio handshake signal, and a streaming media signal. The audio handshake signal coordinates the transmission of the streaming media signal. The streaming media signal of the streaming signal includes one or more QR codes, one or more color images, and one or more video segments.

In certain embodiments, an HDMI interface is installed between the second interface of the streaming signal CODEC and the first interface of the streaming signal transceiver of the secure digital communication device. The streaming signal is transmitted over the HDMI interface. The audio handshake signal of the streaming signal is transmitted through an audio channel of the HDMI interface. The streaming media signal of the streaming signal is transmitted through a display data channel of the HDMI interface.

These and other aspects of the present disclosure will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the present disclosure, and features and benefits thereof, and together with the written description, serve to explain the principles of the present invention. Wherever possible, the same reference numbers are used throughout the drawings to refer to the same or like elements of an embodiment, and wherein:

FIG. 5 shows a frequency combinations of a dual-tone multi-frequency (DTMF) signaling used in audio handshake signal to coordinate transmission of the streaming media signal according to certain embodiments of the present disclosure;

FIG. 8 shows a text based patient report as an exemplary first digital content to be transmitted over the internet using the secure digital communication devices according to certain embodiments of the present disclosure;

DETAILED DESCRIPTION

Figure 1:
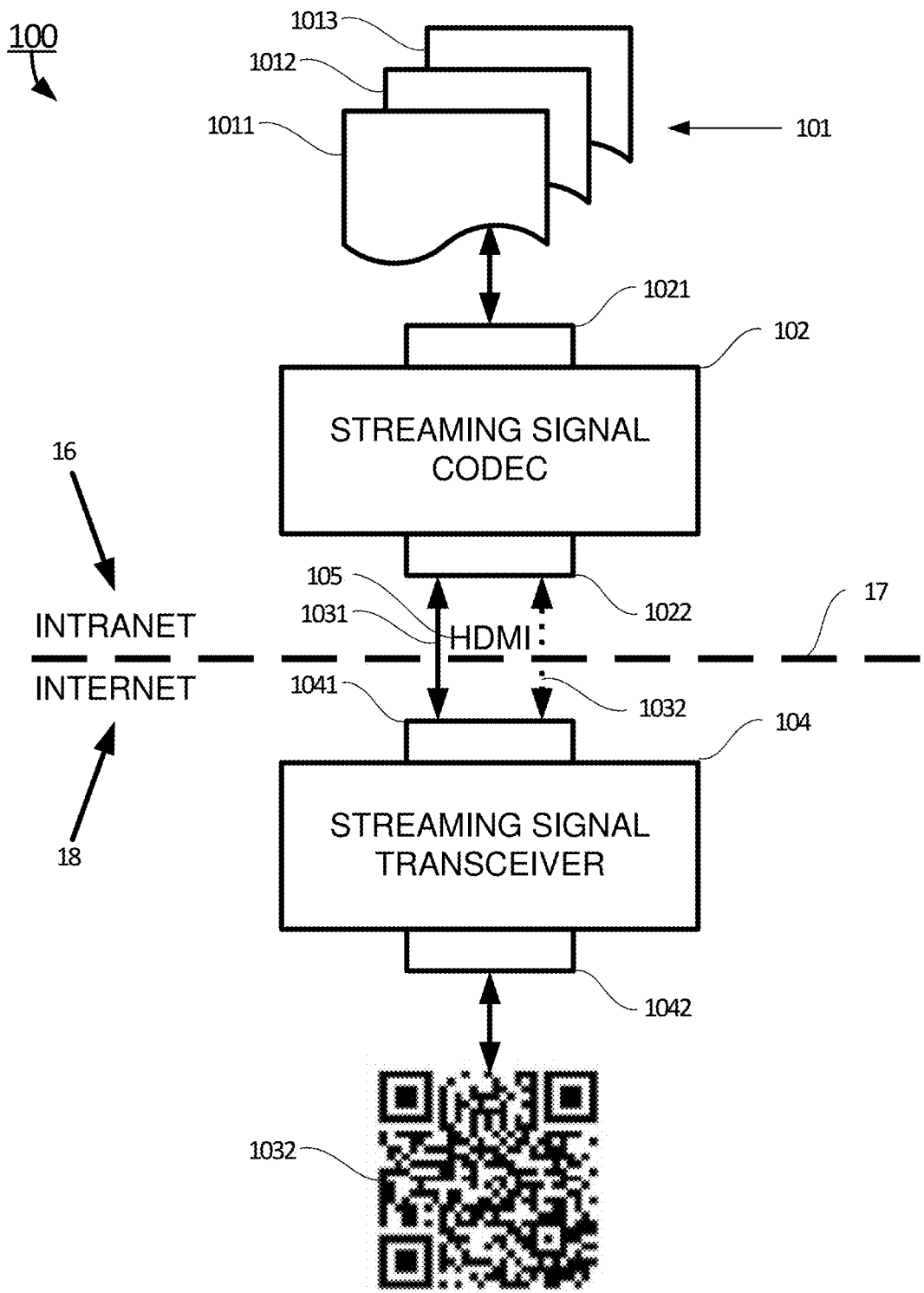
FIG. 1 shows a block diagram of a secure digital communication device according to certain embodiments of the present disclosure.

The present disclosure is more particularly described in the following examples that are intended as illustrative only since numerous modifications and variations therein will be apparent to those skilled in the art. Various embodiments of the disclosure are now described in detail. Referring to the drawings, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present disclosure. Additionally, some terms used in this specification are more specifically defined below.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "plurality" means two or more.

As used herein, the terms "comprising," "including," "carrying," "having," "containing," "involving," and the like are to be understood to be open-ended, i.e., to mean including but not limited to.

As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

As used herein, the term PACS refers to picture archiving and communication system. The term ARP refers to address resolution protocol. The term MITM refers to Man-in-the-Middle. The term QR code refers to a two-dimensional version of the barcode, typically made up of black and white pixel patterns. The term HDMI refers to High-Definition Multimedia Interface for transmitting uncompressed video signal and compressed or uncompressed digital audio signal over HDMI-compliant sources.

As used herein, streaming media protocols include:
RTSP: Real Time Streaming Protocol;
RTMP: Real Time Messaging Protocol;
webRTC: Web Real Time Communication;
HLC: HTTP Live Streaming;
LL-HLS: low-Latency HTTP Live Streaming;
DASH: Dynamic Adaptive Streaming over HTTP, and
SRT: Secure Reliable Transport.
DTMF: Dual-Tone Multi-Frequency Signaling.

The streaming media protocols described above use TCP (Transport Control Protocol) and UDP (User Datagram Protocol) for transport over the internet. TCP Protocol is used mainly for point-to-point data streaming, while UDP is used mainly on one-to-more points data streaming.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The present disclosure will now be described more fully hereinafter with reference to the accompanying drawings FIGS. 1 through 13, in which embodiments of the disclosure are shown. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. Like numbers refer to like elements throughout.

Figure 2:
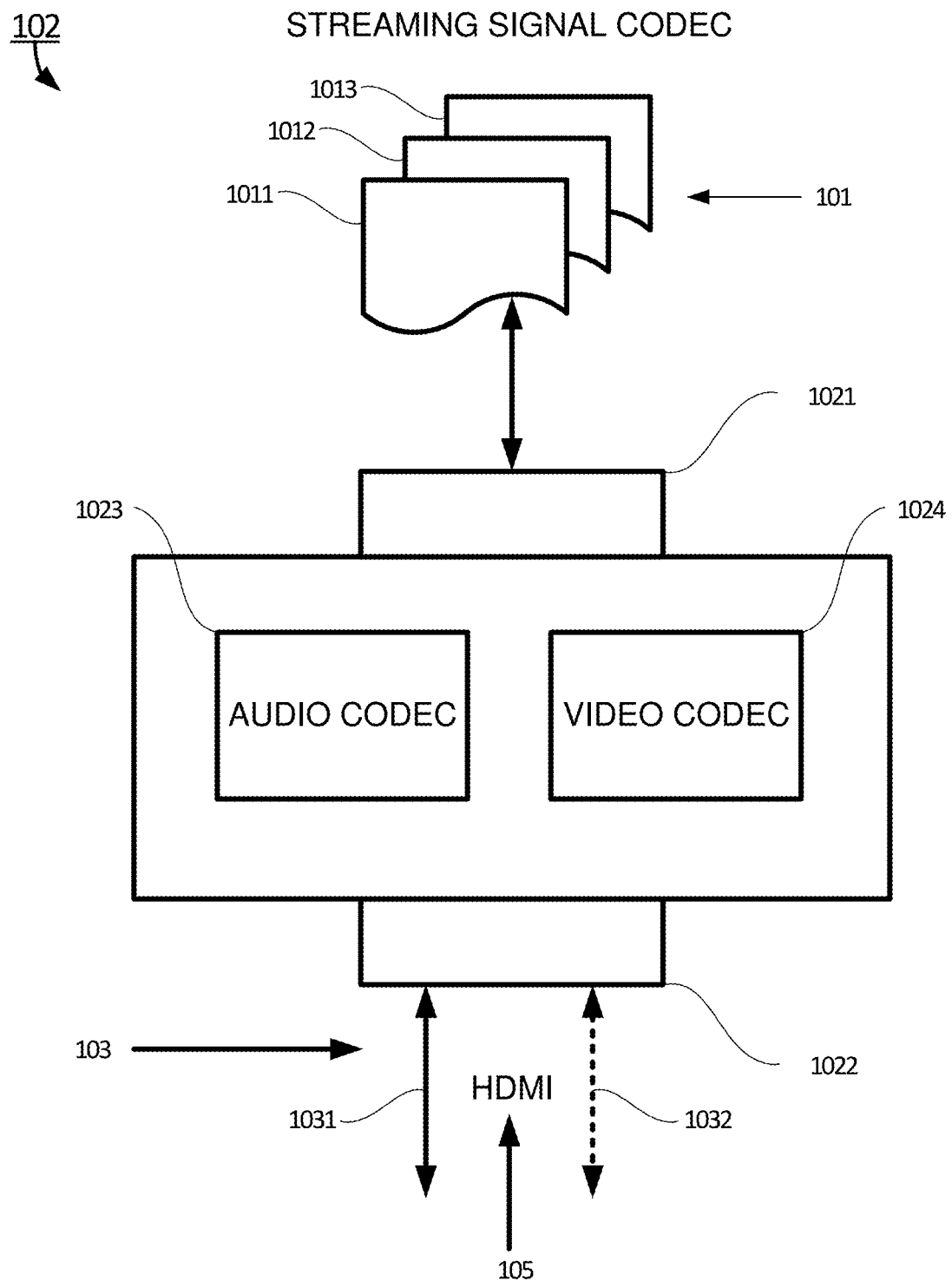
FIG. 2 shows a block diagram of a streaming signal CODEC of the secure digital communication device according to certain embodiments of the present disclosure.

In one aspect, the present disclosure relates to a secure digital communication device 100, as shown in FIG. 1. In certain embodiments, the secure digital communication device 100 includes: a streaming signal CODEC 102, and a streaming signal transceiver 104. As shown in FIG. 2, the streaming signal CODEC 102 includes an Audio CODEC (coder/decoder) 1023, and a Video CODEC 1024. The Audio CODEC 1023 includes: AAC, AAC-LC, HE-AAC+, v1 & v2, MP3, Speex, Opus, and Vorbis. The Video CEDEC 1024 includes: H.264, H.265, VP8, and VP9. The streaming media data is transported using TCP (Transport Control Protocol) and UDP (User Datagram Protocol) protocols. TCP is used mainly for point-to-point data streaming, and UDP is used mainly on one-to-more points data streaming.

Many streaming media protocols may be used for streaming media transmission over the internet. These streaming media protocols include: RTSP (Real-Time Streaming Protocol), RTMP (Real-Time Messaging Protocol), webRTC (Web Real-Time Communication), HLC (HTTP Live Streaming), LL-HLS (low-Latency HTTP Live Streaming), DASH (Dynamic Adaptive Streaming over HTTP), and SRT (Secure Reliable Transport).

In certain embodiments, as shown in FIG. 1, the streaming signal CODEC 102 includes a first interface 1021 and a second interface 1022. The first interface 1021 of the streaming signal CODEC 102 receives one or more incoming digital contents 101 for the streaming signal CODEC 102 to encode the digital contents 101 to a streaming signal 103. The streaming signal CODEC 102 decodes a streaming signal 103 from the second interface 1022 and generates one or more digital contents 101 for output through the first interface 1021 of the streaming signal CODEC 102. The streaming signal transceiver 104 also includes a first interface 1041 and a second interface 1042. The first interface 1041 of the streaming signal transceiver 104 receives the streaming signal 103 from the second interface 1022 of the streaming signal CODEC 102 and transmits the streaming signal 103 received through the second interface 1042 of the streaming signal transceiver 104 over an internet 18. The second interface 1042 of the streaming signal transceiver 104 receives the streaming signal 103 from the internet 18, and transmits the streaming signal 103 received through the first interface 1041 of the streaming signal transceiver 104.

In certain embodiments, the secure digital communication device 100 is installed between an intranet 16 and the internet 18 over a firewall 17 to form a physical isolation of the intranet 16 and the internet 18.

In certain embodiments, when a streaming signal CODEC 102 of a first secure digital communication device 1001 of a first workstation 2001 receives a set of digital contents 101 from the intranet 16 through a first interface 1021, the streaming signal CODEC 102 of the first secure digital communication device 1001 is encoded by the streaming signal CODEC 102 of the first secure digital communication device 1001 of the first workstation 2001 to the streaming signal 103, and transmitted by the streaming signal transceiver 104 of the first secure digital communication device 1001 of the first workstation 2001 to the streaming signal transceiver 104 of the second secure digital communication device 1002 of the second workstation 2002 over the internet 18.

Figure 10:
FIG. 10 shows a color ultrasonic image collected through an ultrasonic diagnostic clinic as an exemplary second digital content, encoded by the secure digital communication device and transmitted over the internet according to certain embodiments of the present disclosure.

In certain embodiments, as shown in FIGS. 1 and 2, the set of digital contents 101 includes: a first digital content 1011, a second digital content 1012, a third digital content 1013, and any combination of these digital contents. The first digital content includes: a word document, a spread sheet document, a power point presentation document, a PDF document, a text document. FIG. 8 shows an exemplary text based electronic file for applying an ultrasonic examination as an example of the first digital content 1011. The second digital content includes: a still image, a color image, and a two-dimensional design. FIG. 10 shows an exemplary ultrasonic image of an ultrasonic examination as an example of the second digital content 1012. The third digital content 1013 includes: one or more video segments (unable to show in the drawings) may include one or more color images (second digital content 1012), as well as one or more video segments.

In certain embodiments, the streaming signal CODEC 102 of the first secure digital communication device 1001 of the first workstation 2001 (1) encodes the first digital content 1011 to the streaming signal 103 having the audio handshake signal 1031 and a QR code 10321, (2) encodes the second digital content 1012 to the streaming signal 103 having the audio handshake signal 1031 and a color image 10322, and (3) encodes the third digital content 1013 to the streaming signal 103 having the audio handshake signal 1031 and a video segment 10323, and the streaming signal transceiver 104 of the first secure digital communication device 1001 of the first workstation 2001 transmits the encoded streaming signal 103 to the streaming signal transceiver 104 of the second secure digital communication device 1002 of the second workstation 2002 over the internet 18.

In certain embodiments, the streaming signal transceiver 104 of the second secure digital communication device 1002 of the second workstation 2002 receives the encoded streaming signal 103 from the streaming signal transceiver 104 of the first secure digital communication device 1001 of the first workstation 2001 over the internet 18, and the streaming signal CODEC 102 of the second secure digital communication device 1002 of the second workstation 2002 decodes the received streaming signal 103 into the first digital content 1011, the second digital content 1012, and the third digital content 1013, according to the encoded streaming signal 103 received, and stores the decoded set of digital contents 101 in the second workstation 2002.

In certain embodiments, an HDMI interface 105 is installed between the second interface 1022 of the streaming signal CODEC 102 and the first interface 1041 of the streaming signal transceiver 104 of the secure digital communication device 100. The streaming signal 103 is transmitted over the HDMI interface 105. The audio handshake signal 1031 of the streaming signal 103 is transmitted through an audio channel of the HDMI interface 105. The streaming media signal 1032 is transmitted through a display data channel of the HDMI interface 105.

Figure 3:
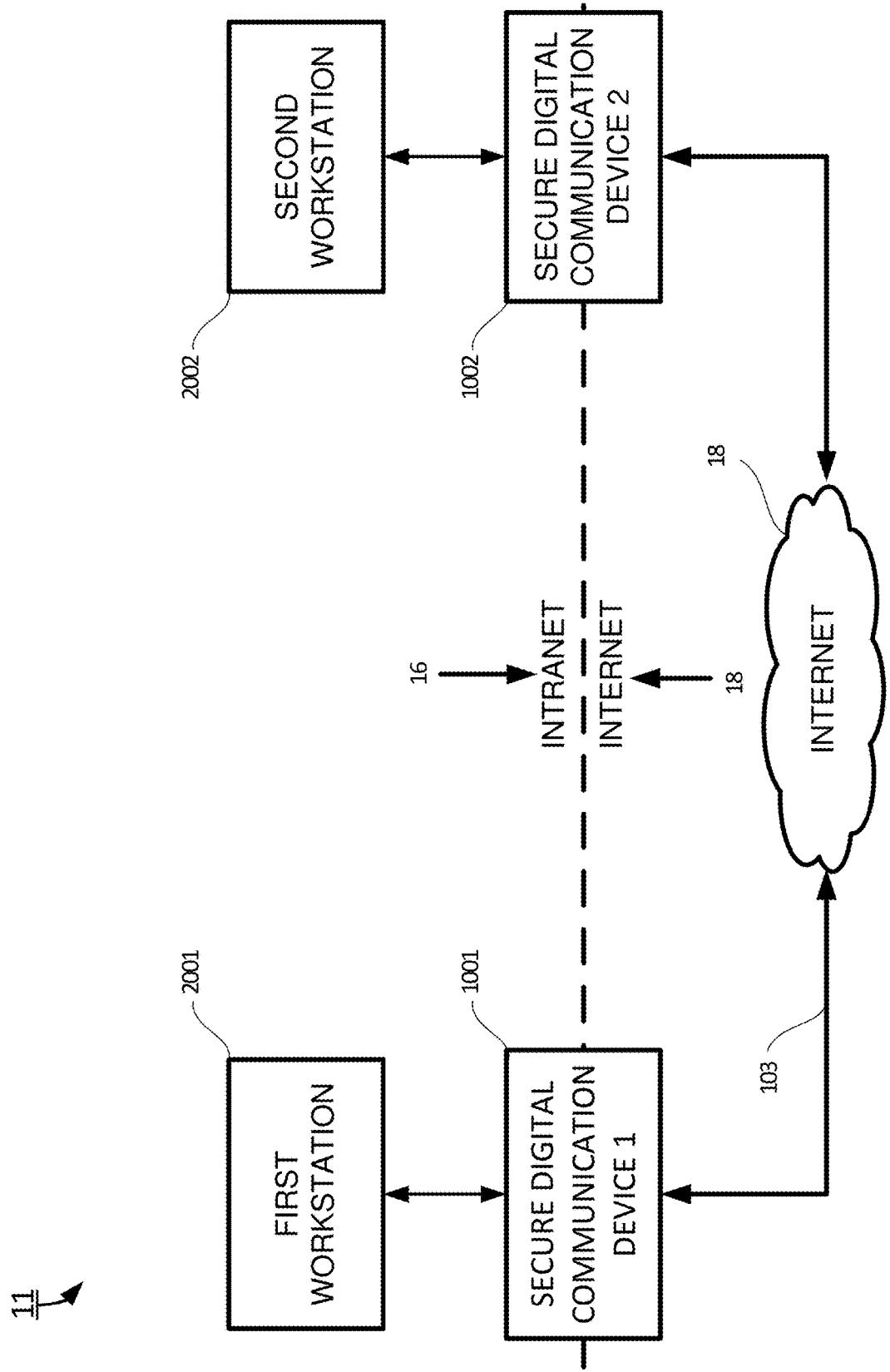
FIG. 3 shows a block diagram of secure communication between a first workstations and a second workstation using secure digital communication devices according to certain embodiments of the present disclosure.

In certain embodiments, as shown in FIG. 3, a block diagram of point-to-point secure digital communication system 11 between a first workstation 2001 and a second workstation 2002 using secure digital communication devices 1001 and 1002, respectively, are shown according to certain embodiments of the present disclosure.

In certain embodiments, when the streaming signal CODEC 102 of a first secure digital communication devices 1001 of the first workstation 2001 receives a set of digital contents 101 from the intranet 16 through the first interface 1021, the streaming signal CODEC 102 of the first secure digital communication devices 1001 encodes the set of digital contents 101 received into a streaming signal 103, and transmits the streaming signal 103 through the second interface 1022 of the streaming signal CODEC 102 of the first secure digital communication devices 1001, via an HDMI interface 150 of the first secure digital communication devices 1001, to the first interface 1041 of the streaming signal transceiver 104 of the first secure digital communication devices 1001. The streaming signal transceiver 104 of the first secure digital communication devices 1001 transmits the streaming signal 103 through the second interface 1042 to a second interface 1042 of a streaming signal transceiver 104 of a second secure digital communication device 1002 of a second workstation 2002 over the internet 18.

In certain embodiments, when the streaming signal transceiver 104 of the second secure digital communication device 1002 receives the streaming signal 103 through the second interface 1042 of the streaming signal transceiver 104 of the second secure digital communication device 1002 over the internet 18, the streaming signal transceiver 104 of the second secure digital communication device 1002 transmits the streaming signal 103 through the first interface 1041 of the streaming signal transceiver 104 of the second secure digital communication device 1002, via an HDMI interface 150 of the second secure digital communication device 1002, to a second interface 1022 of a streaming signal CODEC 102 of the second secure digital communication device 1002, the streaming signal CODEC 102 of the second secure digital communication device 1002 decodes the streaming signal 103 to the set of digital contents 101, and stores the set of digital contents 101 decoded in the second workstation 2002.

In certain embodiments, the streaming signal is transmitted over the internet using at least one of following protocols: RTSP (Real-Time Streaming Protocol), RTMP (Real-Time Messaging Protocol), webRTC (Web Real-Time Communication), HLC (HTTP Live Streaming), LL-HLS (low-Latency HTTP Live Streaming), DASH (Dynamic Adaptive Streaming over HTTP), and SRT (Secure Reliable Transport), and any combination thereof.

Figure 4:
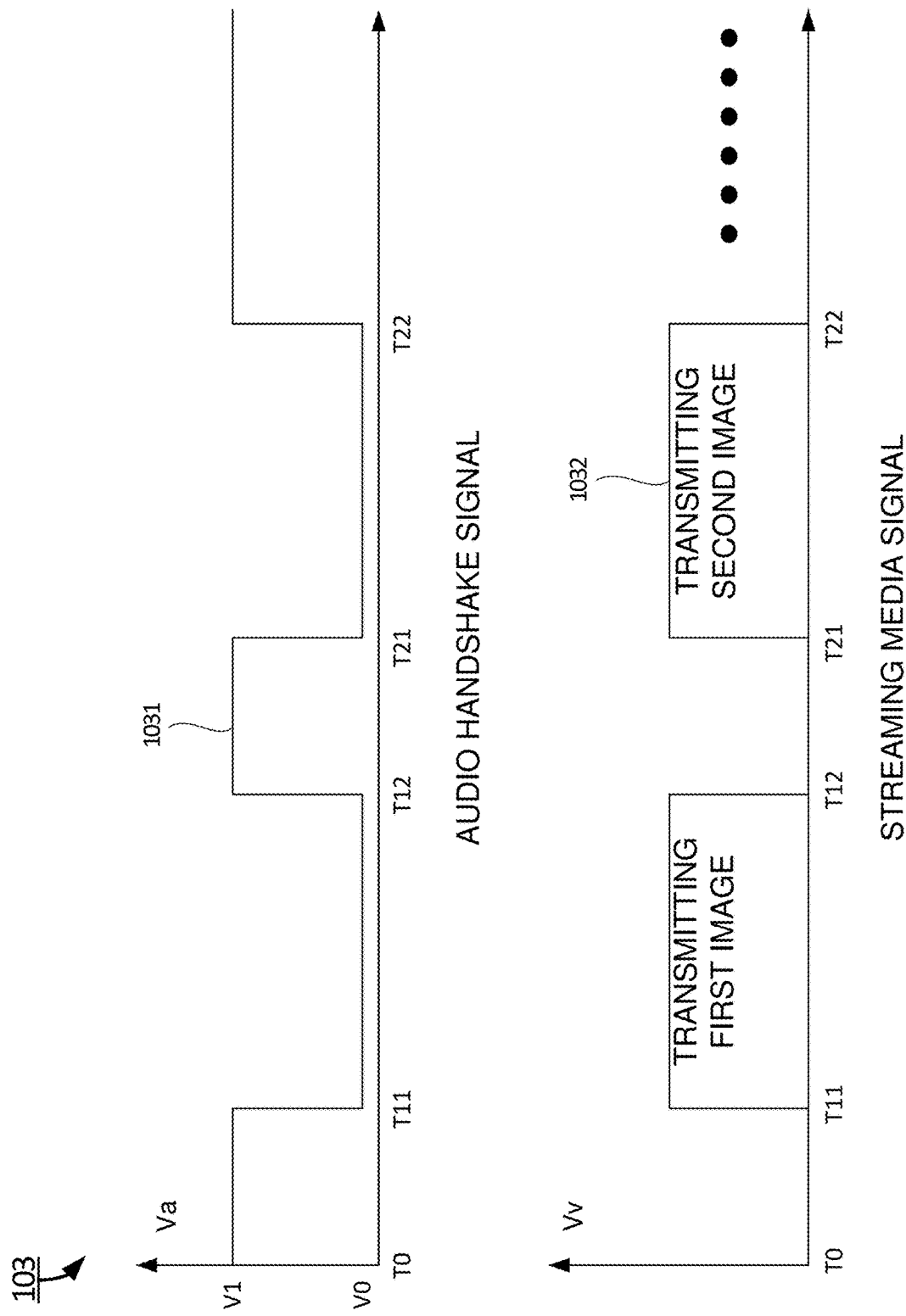
FIG. 4 shows functional waveforms of an audio handshake signal and a streaming media signal of a streaming signal according to one of streaming media protocols during transmission of the streaming signal according to certain embodiments of the present disclosure.

In certain embodiments, as shown in FIG. 4, the streaming signal 103 includes an audio handshake signal 1031, and a streaming media signal 1032.

Figure 9:
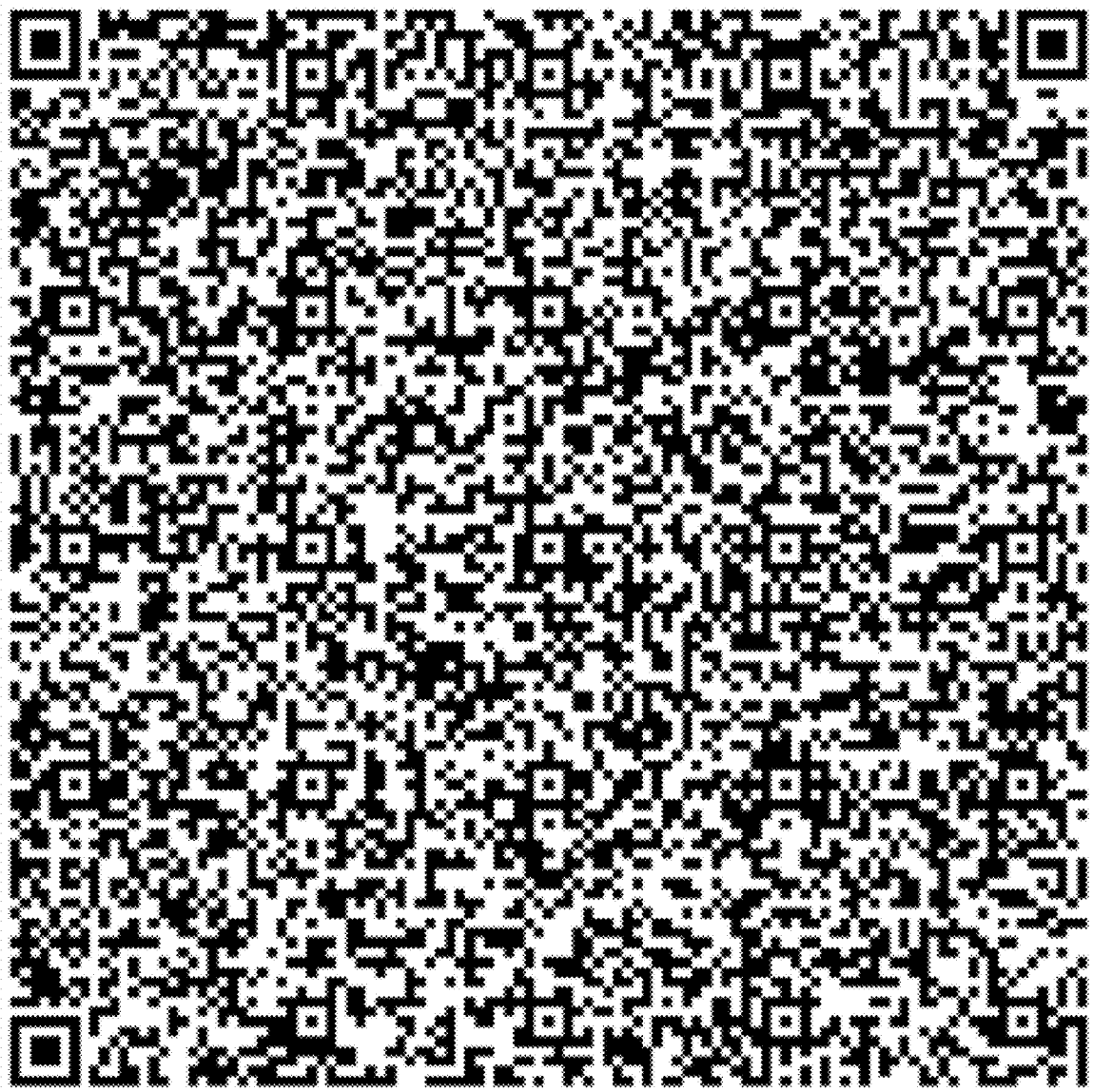
FIG. 9 shows an exemplary QR code representing the patient report shown in FIG. 8, encoded by the secure digital communication device and transmitted over the internet according to certain embodiments of the present disclosure.

In certain embodiments, the streaming signal 103 includes: an audio handshake signal 1031 and a streaming media signal 1032. The streaming signal 103 is transmitted between a first workstation 2001 and a second workstation 2002 in the secure digital communication system 10. The audio handshake signal 1031 coordinates the transmission of the streaming media signal 1032. The streaming media signal 1032 of the streaming signal 103 includes one or more QR codes 10321 as shown in FIG. 9, one or more color images 10322, as shown in FIG. 10, and one or more video segments 10323 (not shown). The audio handshake signal 1031 includes a dual-tone multi-frequency (DTMF) signaling, and the streaming media signal 1032 includes a set of digital streaming media.

In certain embodiments, as shown in FIG. 4, when the audio handshake signal 1031 changes from high voltage to low voltage in T11, the streaming signal transceiver 104 of the first secure digital communication devices 1001 of the first workstation 2001 transmits the streaming media signal 1032 (first image) of the streaming signal 103 through the second interface 1042 to the second interface 1042 of the streaming signal transceiver 104 of the second secure digital communication device 1002 of the second workstation 2002 over the internet 18. When the audio handshake signal 1031 changes from low voltage to high voltage in T12, the streaming signal transceiver 104 of the first secure digital communication devices 1001 of the first workstation 2001 completes the transmission of the streaming media signal 1032 (first image) of the streaming signal 103 through the second interface 1042 to the second interface 1042 of the streaming signal transceiver 104 of the second secure digital communication device 1002 of the second workstation 2002 over the internet 18.

When the audio handshake signal 1031 changes from high voltage to low voltage in T21, the streaming signal transceiver 104 of the first secure digital communication devices 1001 of the first workstation 2001 transmits the streaming media signal 1032 (second image) of the streaming signal 103 through the second interface 1042 to the second interface 1042 of the streaming signal transceiver 104 of the second secure digital communication device 1002 of the second workstation 2002 over the internet 18. When the audio handshake signal 1031 changes from low voltage to high voltage in T22, the streaming signal transceiver 104 of the first secure digital communication devices 1001 of the first workstation 2001 completes the transmission of the streaming media signal 1032 (second image) of the streaming signal 103 through the second interface 1042 to the second interface 1042 of the streaming signal transceiver 104 of the second secure digital communication device 1002 of the second workstation 2002 over the internet 18.

In certain embodiments, as shown in FIG. 5, the dual-tone multi-frequency (DTMF) signaling are adopted from standard telecommunication system such that the usage of this standard signaling made the system easy to implement. The DTMF signaling includes: an A tone having a low frequency of 697 Hz and a high frequency of 1633 Hz, a B tone having a low frequency of 770 Hz and a high frequency of 1633 Hz, a C tone having a low frequency of 852 Hz and a high frequency of 1633 Hz, and a D tone having a low frequency of 941 Hz and a high frequency of 1633 Hz.

Figure 6:
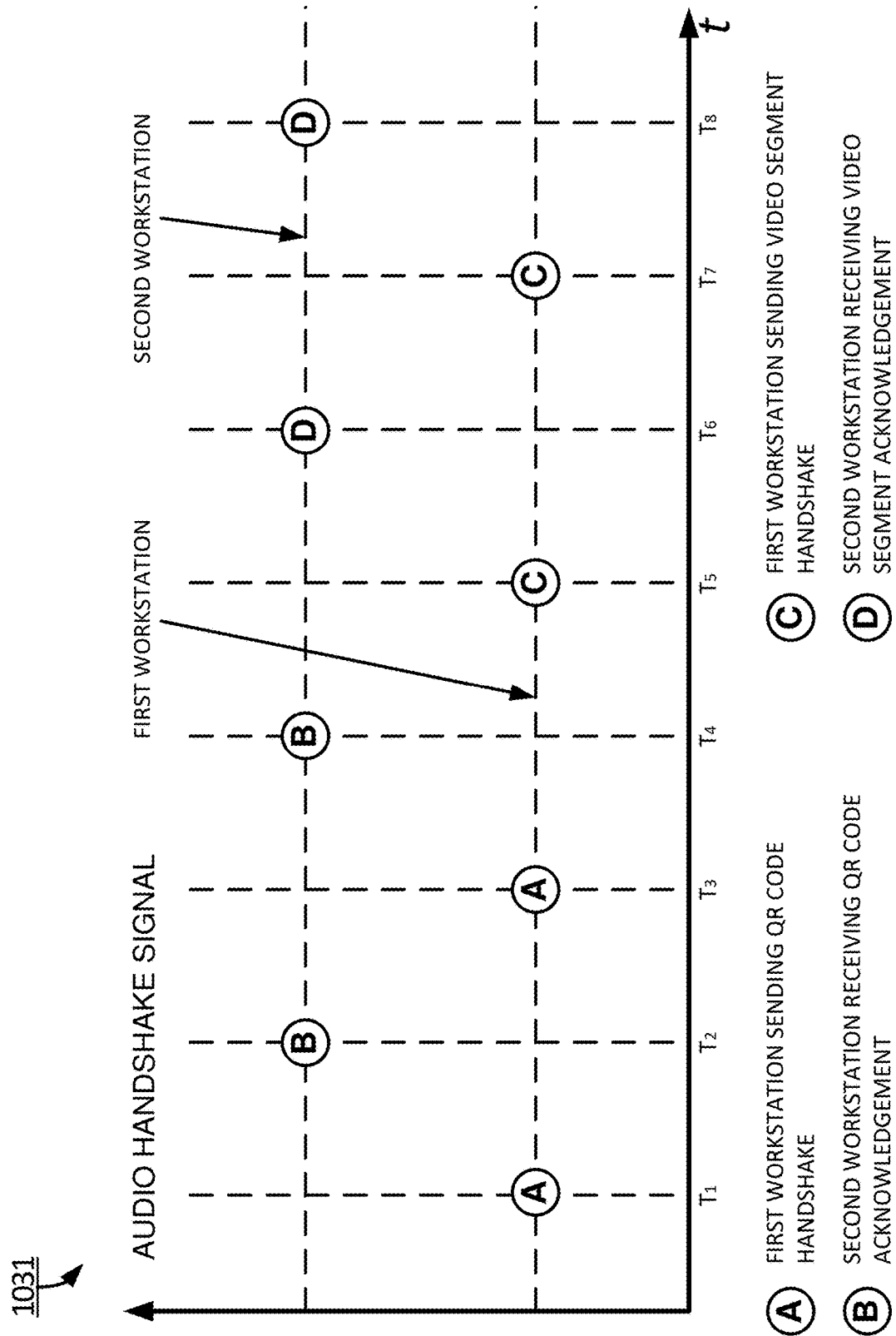
FIG. 6 shows a time sequence when the first workstation transmits QR codes streaming signal and color images and streaming media signal according to certain embodiments of the present disclosure.

In certain embodiments, as shown in FIG. 6, the A tone from the first workstation 2001 to the second workstation 2002 at time T1 is a handshake signal indicating that the first workstation 2001 sends a first QR code to the second workstation 2002. The B tone from the second workstation 2002 at T2 to the first workstation 2001 is an acknowledgement signal indicating that the second workstation 2002 received the first QR code from the first workstation 2001. The A tone from the first workstation 2001 to the second workstation 2002 at time T3 is a handshake signal indicating that the first workstation 2001 sends a second QR code to the second workstation 2002. The B tone from the second workstation 2002 at T4 to the first workstation 2001 is an acknowledgement signal indicating that the second workstation 2002 received the second QR code from the first workstation 2001.

In certain embodiments, the C tone from the first workstation 2001 to the second workstation 2002 at time T5 is a handshake signal indicating the first workstation 2001 sends a first video segment to the second workstation 2002. The D tone from the second workstation 2002 at time T6 to the first workstation 2001 is an acknowledgement signal indicating that the second workstation 2002 received the first video segment from the first workstation 2001. The C tone from the first workstation 2001 to the second workstation 2002 at time T7 is a handshake signal indicating the first workstation 2001 sends a second video segment to the second workstation 2002. The D tone from the second workstation 2002 at time T8 to the first workstation 2001 is an acknowledgement signal indicating that the second workstation 2002 received the second video segment from the first workstation 2001.

Figure 7:
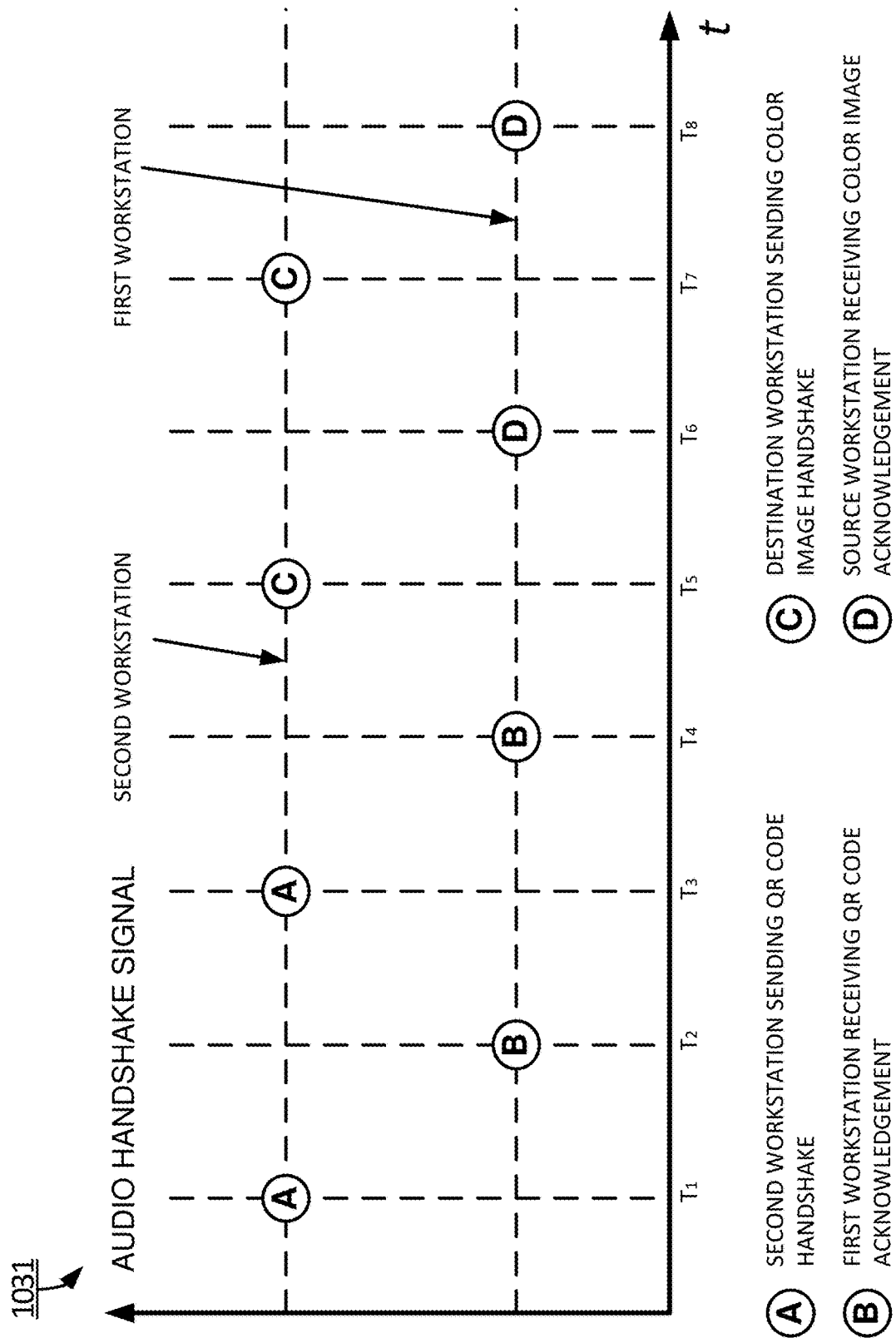
FIG. 7 shows a time sequence when the first workstation receives QR codes streaming signal, color images and streaming media signal according to certain embodiments of the present disclosure.

In certain embodiments, a video segment may include one or more color images. Thus, the C tone and the D tone are used in the audio handshake signal 1031 of the of the streaming signal 103 to coordinate the transmission of the second digital contents 1012 and the third digital contents 1013. As shown in FIG. 7, the A tone from the second workstation 2002 to the first workstation 2001 at time $T_1$ is a handshake signal indicating that the second workstation 2002 sends a first QR code to the first workstation 2001. The B tone from the first workstation 2001 at $T_2$ to the second workstation 2002 is an acknowledgement signal indicating that the first workstation 2001 received the first QR code from the second workstation 2002. The A tone from the second workstation 2002 to the first workstation 2001 at time $T_3$ is a handshake signal indicating that the second workstation 2002 sends a second QR code to the first workstation 2001. The B tone from the first workstation 2001 at $T_4$ to the second workstation 2002 is an acknowledgement signal indicating that the first workstation 2001 received the second QR code from the second workstation 2002.

In certain embodiments, the C tone from the second workstation 2002 to the first workstation 2001 at time $T_5$ is a handshake signal indicating the second workstation 2002 sends a first color image to the first workstation 2001. The D tone from the first workstation 2001 at time $T_6$ to the second workstation 2002 is an acknowledgement signal indicating that the first workstation 2001 received the first color image from the second workstation 2002. The C tone from the second workstation 2002 to the first workstation 2001 at time $T_7$ is a handshake signal indicating the second workstation 2002 sends a second color image to the first workstation 2001. The D tone from the first workstation 2001 at time $T_8$ to the second workstation 2002 is an acknowledgement signal indicating that the first workstation 2001 received the second color image from the second workstation 2002.

In certain embodiments, in a private network such as the intranet 16, physical connections, such as CAT-5 cable connectors, and USB connectors, between the private network and the open internet are not allowed. The secure digital communication device 100 forms a bridge and a physical isolation between the intranet 16 and the internet 18, and digital contents 101 are converted to QR codes and transported through the secure digital communication device 100 to avoid MITM attacks and introductions of various computer virus.

Figure 11:
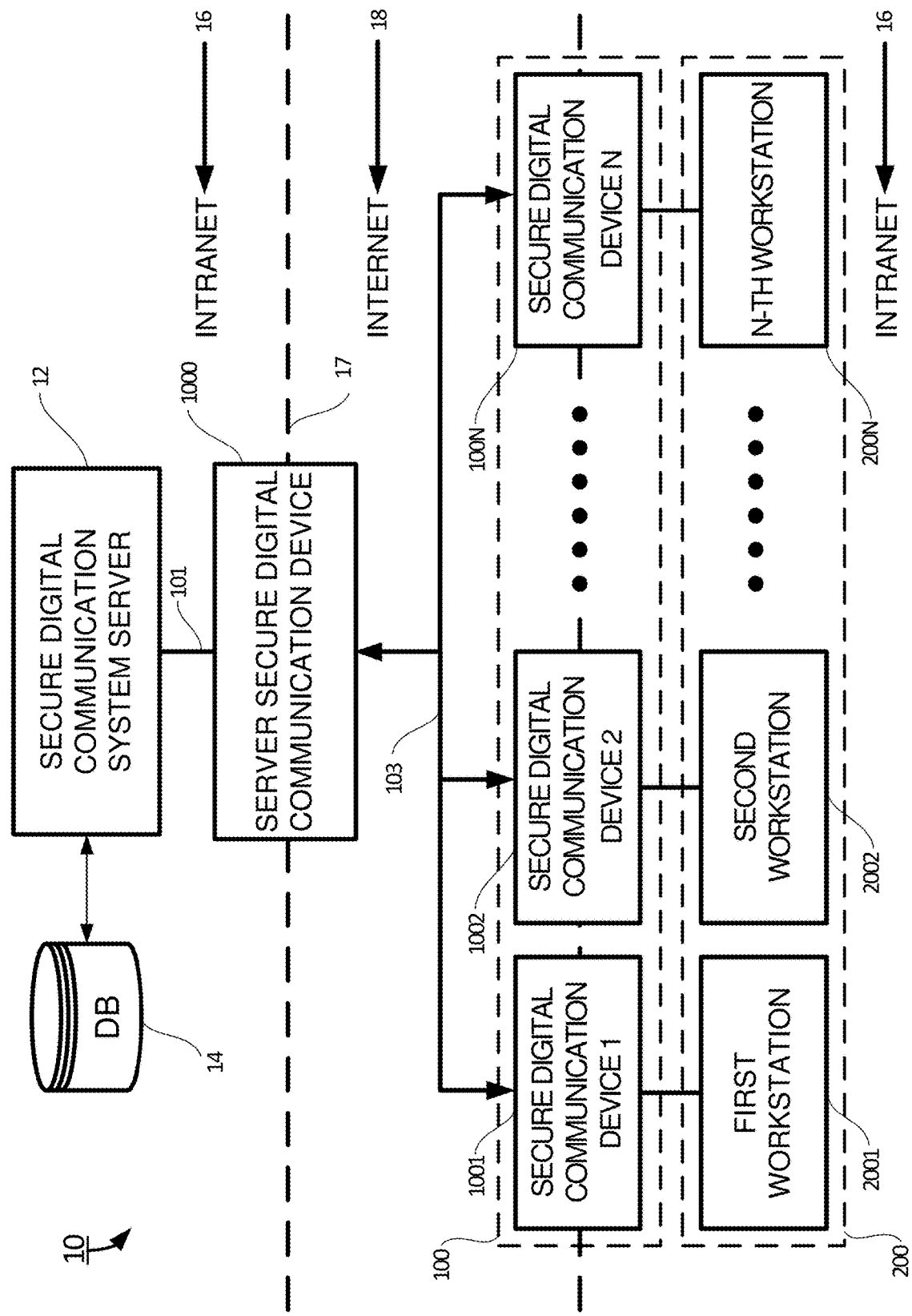
FIG. 11 shows a block diagram of a secure digital communication system when multiple workstations are connected to a secure digital communication system server using the secure digital communication devices according to certain embodiments of the present disclosure.

In another aspect, the present disclosure relates to a secure digital communication system 10. In certain embodiments, as shown in FIG. 11, the secure digital communication system 10 includes: a secure digital communication system server 12, a group of workstations 200, and each workstation 200 includes a secure digital communication device 100. The secure digital communication system server 12 is connected to a database 14, and a server secure digital communication device 1000. Each of the group of workstations 200 is installed in an intranet 16, the workstations 200 are connected to the secure digital communication system server 12 over an internet 18. Each secure digital communication device 100 connects a corresponding workstation 200 to the server secure digital communication device 1000 of the secure digital communication system server 12 to facilitate secure communication among the group of workstations 200 and the secure digital communication system server 12.

In certain embodiments, each of the secure digital communication devices 100 and the server secure digital communication device 1000 includes: a streaming signal CODEC 102 and a streaming signal transceiver 104. The streaming signal CODEC 102 includes a first interface 1021 and a second interface 1022. The streaming signal transceiver 104 includes a first interface 1041 and a second interface 1042. The secure digital communication device 100 is installed in a workstation between the intranet 16 and the internet 18 over a firewall 17 to form a physical isolation of the intranet 16 and the internet 18.

In certain embodiments, when a streaming signal CODEC 102 of a first secure digital communication device 1001 of a first workstation 2001 receives a set of digital contents 101 from the intranet 16 through the first interface 1021, the streaming signal CODEC 102 of the first secure digital communication device 1001 encodes the set of digital contents 101 received into a streaming signal 103, transmits the streaming signal 103 through the second interface 1022 of the streaming signal CODEC 102 of the first secure digital communication device 1001 to the first interface 1041 of the streaming signal transceiver 104 of the first secure digital communication device 1001. The streaming signal transceiver 104 of the first secure digital communication device 1001 transmits the streaming signal 103 through the second interface 1042 to a second interface 1042 of a streaming signal transceiver 104 of a second secure digital communication device 1002 of a second workstation 2002 over the internet 18.

In certain embodiments, when the streaming signal transceiver 104 of the second secure digital communication device 1002 receives the streaming signal 103 through the second interface 1042 over the internet 18, the streaming signal transceiver 104 of the second secure digital communication device 1002 transmits the streaming signal 103 through a first interface 1041 of the streaming signal transceiver 104 of the second secure digital communication device 1002 to a second interface 1022 of the streaming signal CODEC 102 of the second secure digital communication device 1002, the streaming signal CODEC 102 of the second secure digital communication device 1002 decodes the streaming signal 103 to the set of digital contents 101, and stores the set of digital contents 101 decoded in the second workstation 2002.

In certain embodiments, the streaming signal 103 is transmitted over the internet using at least one of following protocols: RTSP (Real-Time Streaming Protocol), RTMP (Real-Time Messaging Protocol), webRTC (Web Real-Time Communication), HLC (HTTP Live Streaming), LL-HLS (low-Latency HTTP Live Streaming), DASH (Dynamic Adaptive Streaming over HTTP), and SRT (Secure Reliable Transport), and any combination of these protocols.

In certain embodiments, the set of digital contents 101 includes a word document, a spread sheet document, a power point presentation document, a PDF document, a text document, a still image, a video segment, and any combination thereof.

In certain embodiments, the streaming signal 103 includes an audio handshake signal 1031, and a streaming media signal 1032. The audio handshake signal 1031 coordinates the transmission of the streaming media signal 1032. The streaming media signal 1032 of the streaming signal 103 includes one or more QR codes 10321, one or more color images 10322, and one or more video segments 10323.

In certain embodiments, an HDMI interface 105 is installed between the second interface 1022 of the streaming signal CODEC 102 and the first interface 1041 of the streaming signal transceiver 104 of the secure digital communication device 100. The streaming signal 103 is transmitted over the HDMI interface 105. The audio handshake signal 1031 of the streaming signal 103 is transmitted through an audio channel of the HDMI interface 105. The streaming media signal 1032 of the streaming signal 103 is transmitted through a display data channel of the HDMI interface 105.

Figure 12:
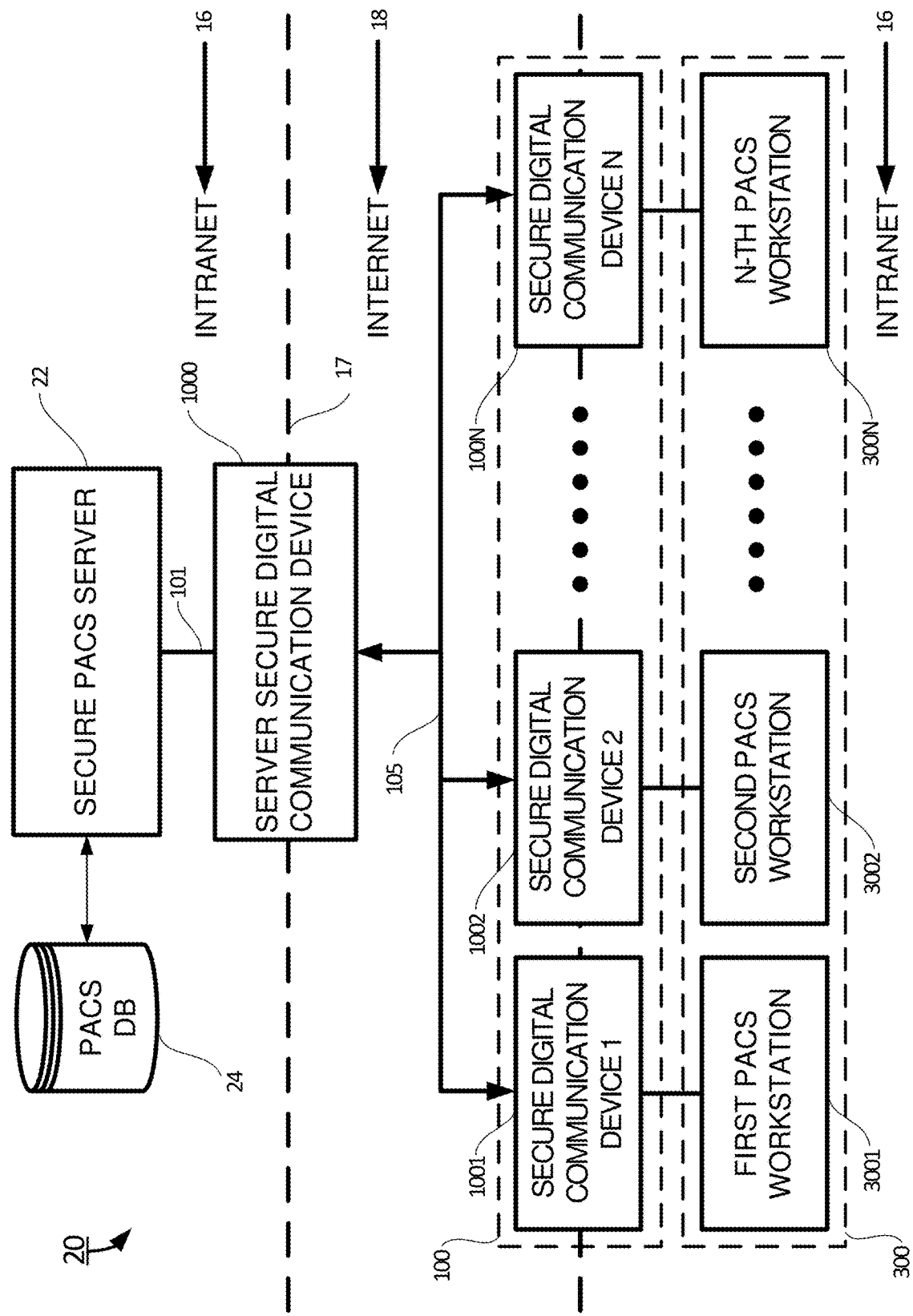
FIG. 12 shows a block diagram of a secure Picture Archiving and Communication System (PACS) when multiple workstations are connected to a secure PACS server using the secure digital communication devices according to certain embodiments of the present disclosure.

In yet another aspect, the present disclosure relates to a secure Picture Archiving and Communication System (PACS) 20, as shown in FIG. 12. In certain embodiments, the secure PACS 20 includes: a PACS server 22, a group of PACS workstations 300 installed in an intranet 16, and a group of secure digital communication devices 100, each of the group of the secure digital communication devices 100 is connected to a PACS workstation 300$x$. For instance, a secure digital communication device 1 1001 is connected to a first PACS workstation 3001, a secure digital communication device 2 1002 is connected to a second PACS workstation 3002, . . . , and a secure digital communication device N 100N is connected to a N-th PACS workstation 300N. The PACS server 22 is connected to a PACS database 24 and a server secure digital communication device 1000. The group of PACS workstations 300 are connected to the PACS server 22 over an internet 18. Each of the group of secure digital communication devices 100 connects to a corresponding PACS workstation 300$x$ to the server secure digital communication device 1000 of the PACS server 22 to facilitate secure digital communication among the group of PACS workstations 300$x$ and the PACS server 22 over the server secure digital communication device 1000 and the group of the secure digital communication devices 100.

In certain embodiments, each of the group of secure digital communication devices 100 and the server secure digital communication device 1000 includes: a streaming signal CODEC 102, and a streaming signal transceiver 104. The streaming signal CODEC 102 includes a first interface 1021 and a second interface 1022. The streaming signal transceiver 104 includes a first interface 1041 and a second interface 1042. The secure digital communication device 100 is installed between the intranet 16 and the internet 18 over a firewall 17 to form a physical isolation of the intranet 16 and the internet 18.

In certain embodiments, when a streaming signal CODEC 102 of a first secure digital communication device 1001 of a first PACS workstation 3001 receives a set of PACS contents 101 from the intranet 16 through its first interface 1021, the streaming signal CODEC 102 of the first secure digital communication device 1001 encodes the set of PACS contents 101 into a streaming signal 103, and transmits the streaming signal 103 through the second interface 1022 of the streaming signal CODEC 102 of the first secure digital communication device 1001 to a first interface 1041 of a streaming signal transceiver 104 of the first secure digital communication device 1001. The streaming signal transceiver 104 of the first secure digital communication device 1001 transmits the streaming signal 103 through the second interface 1042 of the streaming signal transceiver 104 of the first secure digital communication device 1001 to a second interface 1042 of a streaming signal transceiver 104 of a second secure digital communication device 1002 of a second PACS workstation 3002 over the internet 18.

In certain embodiments, when the streaming signal transceiver 104 of the second secure digital communication device 1002 of the second PACS workstation 3002 receives the streaming signal 103 through the second interface 1042 over the internet 18, the streaming signal transceiver 104 of the second PACS workstation 3002 transmits the streaming signal 103 through a first interface 1041 of the streaming signal transceiver 104 of the second secure digital communication device 1002 to a second interface 1022 of a streaming signal CODEC 102 of the second secure digital communication device 1002, the streaming signal CODEC 102 of the second secure digital communication device 1002 decodes the streaming signal 103 to the set of PACS contents 101 received, and stores the set of PACS contents 101 decoded in the second PACS workstation 3002.

In certain embodiments, the streaming signal is transmitted over the internet using at least one of following protocols: RTSP (Real-Time Streaming Protocol), RTMP (Real-Time Messaging Protocol), webRTC (Web Real-Time Communication), HLC (HTTP Live Streaming), LL-HLS (low-Latency HTTP Live Streaming), DASH (Dynamic Adaptive Streaming over HTTP), and SRT (Secure Reliable Transport), and any combination thereof.

In certain embodiments, the set of PACS contents 101 includes: a word document, a spread sheet document, a power point presentation document, a PDF document, a text document, a still image, a video segment, and any combination thereof.

In certain embodiments, the streaming signal 103 includes an audio handshake signal 1031, and a streaming media signal 1032. The audio handshake signal 1031 coordinates the transmission of the streaming media signal 1032. The streaming media signal 1032 of the streaming signal 103 includes one or more QR codes 10321, one or more color images 10322, and one or more video segments 10323.

In certain embodiments, an HDMI interface 105 is installed between the second interface 1022 of the streaming signal CODEC 102 and the first interface 1041 of the streaming signal transceiver 104 of each secure digital communication device 100. The streaming signal 103 is transmitted over the HDMI interface 105. The audio handshake signal 1031 of the streaming signal 103 is transmitted through an audio channel of the HDMI interface 105. The streaming media signal 1032 of the streaming signal 103 is transmitted through a display data channel of the HDMI interface 105.

Figure 13:
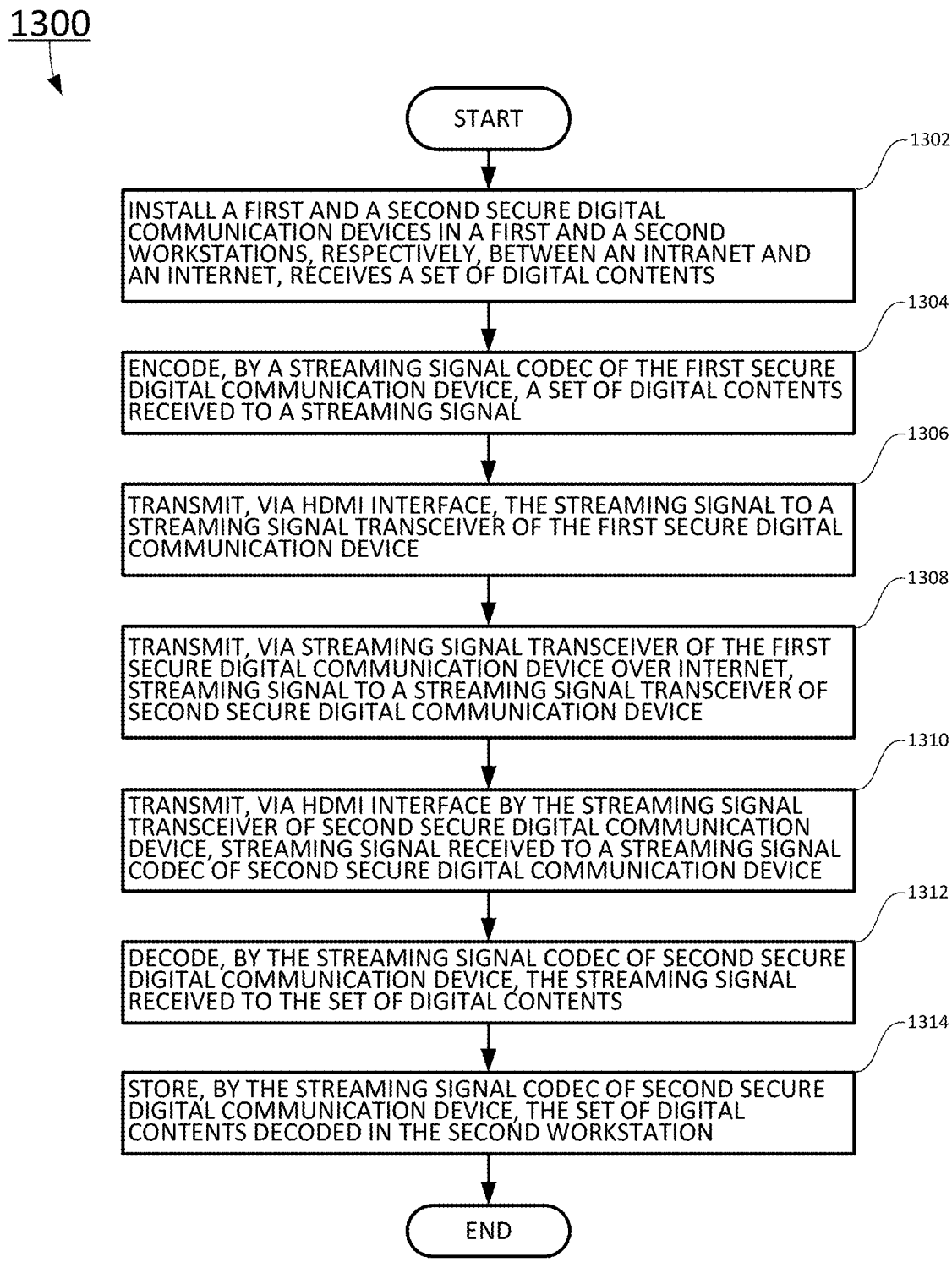
FIG. 13 illustrates a flowchart of a method of securely transmitting a set of digital contents in a secure digital communication system according to certain embodiments of the present disclosure.

In a further aspect, the present disclosure relates to a method of securely transmitting a set of digital contents 101 in a secure digital communication system 10 as shown in FIG. 11. Referring now to FIG. 13, a flow chart 1300 of securely transmitting a set of digital contents 101 in a secure digital communication system 10 is shown according to certain embodiments of the present disclosure.

At block 1302, a user installs a first secure digital communication device 1001 in a first workstation 2001 and a second secure digital communication device 1002 in a second workstation 2002 between an intranet 16 and an internet 18 over a firewall 17. In certain embodiments, the streaming signal CODEC 102 of the first secure digital communication device 1001 of the first workstation 2001 receives a set of digital contents 101 over intranet 16.

In certain embodiments, the set of digital contents 101 includes: a first digital content 1011, a second digital content 1012, a third digital content 1013, and any combination of these digital contents. The first digital content includes: a word document, a spread sheet document, a power point presentation document, a PDF document, a text document. The second digital content includes: a still image, a color image, and a two-dimensional design. The third digital content 1013 includes: one or more video segments.

At block 1304, a streaming signal CODEC 102 of the first secure digital communication device 1001 of the first workstation 2001, encodes the set of digital contents 101 received to a streaming signal 103 having an audio handshake signal 1031 and a streaming media signal 1032. The audio handshake signal 1031 coordinates the transmission of the streaming media signal 1032. The streaming media signal 1032 of the streaming signal 103 includes one or more QR codes 10321 as shown in FIG. 9, one or more color images 10322, as shown in FIG. 10, and one or more video segments 10323 (not shown). The audio handshake signal 1031 includes a dual-tone multi-frequency (DTMF) signaling, and the streaming media signal 1032 includes a set of digital streaming media.

In certain embodiments, encoding the set of digital contents 101 to the streaming signal 103 includes:

encoding the first digital content 1011 to the streaming signal 103 having the audio handshake signal 1031 and a QR code 10321;

encoding the second digital content 1012 to the streaming signal 103 having the audio handshake signal 1031 and a color image 10322; and encoding the third digital content 1013 to the streaming signal 103 having the audio handshake signal 1031 and a video segment 10323.

At block 1306, the streaming signal CODEC 102 of the first secure digital communication device 1001 of the first workstation 2001 transmits, via an HDMI interface 105 of the first secure digital communication device 1001, the streaming signal 103 to a streaming signal transceiver 104 of the first secure digital communication device 1001.

In certain embodiments, transmitting the streaming signal 103 between the streaming signal CODEC 102 and the streaming signal transceiver 104 of the first secure digital communication device 1001 includes:

transmitting the audio handshake signal 1031 through an audio channel of the HDMI interface 105; and transmitting the streaming media signal 1032 through a display data channel of the HDMI interface 105.

At block 1308, the streaming signal transceiver 104 of the first secure digital communication device 1001 of the first workstation 2001 transmits the streaming signal 103 to a streaming signal transceiver 104 of the second secure digital communication device 1002 of the second workstation 2002 over the internet 18.

At block 1310, the streaming signal transceiver 104 of the second secure digital communication device 1002 transmits, via an HDMI interface 105 of the second secure digital communication device 1002, the streaming signal 103 to a streaming signal CODEC 102 of the second secure digital communication device 1002 of the second workstation 2002.

In certain embodiments, transmitting the streaming signal 103 between the streaming signal transceiver 104 and the streaming signal CODEC 102 of the second secure digital communication device 1002 includes:

transmitting the audio handshake signal 1031 through an audio channel of the HDMI interface 105; and transmitting the streaming media signal 1032 through a display data channel of the HDMI interface 105.

At block 1312, the streaming signal CODEC 102 of the second secure digital communication device 1002 of the second workstation 2002 decodes the streaming signal 103 to the set of digital contents 101.

In certain embodiments, decoding the streaming signal 103 to the set of digital contents 101 includes:

decoding the audio handshake signal 1031 and the QR code 10321 to the first digital content 1011;

decoding the audio handshake signal 1031 and the color image 10322 to the second digital content 1012; and decoding the audio handshake signal 1031 and the video segment 10323 to the third digital content 1013.

At block 1314, the streaming signal CODEC 102 of the second secure digital communication device 1002 of the second workstation 2002 stores the set of digital contents 101 decoded in the second workstation 2002.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A secure digital communication device, comprising:
a streaming signal CODEC having a first interface and a second interface; and
a streaming signal transceiver having a first interface and a second interface,
wherein the secure digital communication device is installed in a workstation between an intranet and an internet over a firewall to form a physical isolation of the intranet and the internet, when a streaming signal CODEC of a first secure digital communication device of a first workstation receives a plurality of digital contents from the intranet through the first interface, the streaming signal CODEC of the first secure digital communication device encodes the plurality of digital contents received into a streaming signal, transmits the streaming signal through the second interface of the streaming signal CODEC to a first interface of a streaming signal transceiver of the first secure digital communication device, the streaming signal transceiver of the first secure digital communication device transmits the streaming signal through the second interface to a second interface of a streaming signal transceiver of a second secure digital communication device of a second workstation over the internet, and when the streaming signal transceiver of the second secure digital communication device receives the streaming signal through the second interface over the internet, the streaming signal transceiver of the second secure digital communication device transmits the streaming signal through the first interface of the streaming signal transceiver of the second secure digital communication device to the second interface of the streaming signal CODEC of the second secure digital communication device, the streaming signal CODEC of the second secure digital communication device decodes the streaming signal to the plurality of digital contents, and stores the plurality of digital contents decoded in the second workstation.

2. The secure digital communication device according to claim 1, wherein the plurality of digital contents comprises a word document, a spread sheet document, a power point presentation document, a PDF document, a text document, a still image, a video segment, and any combination thereof.

3. The secure digital communication device according to claim 1, wherein the streaming signal comprises an audio handshake signal, and a streaming media signal.

4. The secure digital communication device according to claim 3, wherein the audio handshake signal coordinates the transmission of the streaming media signal, and streaming media signal of the streaming signal comprises one or more QR codes, one or more color images, and one or more video segments.

5. The secure digital communication device according to claim 4, wherein an HDMI interface is installed between the second interface of the streaming signal CODEC and the first interface of the streaming signal transceiver of the secure digital communication device.

6. The secure digital communication device according to claim 5, wherein the streaming signal is transmitted over the HDMI interface, the audio handshake signal is transmitted through an audio channel of the HDMI interface; and the streaming media signal is transmitted through a display data channel of the HDMI interface.

7. A secure digital communication system, comprising:
a secure digital communication system server, wherein the secure digital communication system server is connected to a database, and a server secure digital communication device;
a plurality of workstations installed in an intranet, wherein the plurality of workstations connects to the secure digital communication system server over an internet; and
a plurality of secure digital communication devices, wherein each of the plurality of secure digital communication devices connects to a corresponding workstation to the server secure digital communication device of the secure digital communication system server to facilitate secure communication among the corresponding workstation and the secure digital communication system server,
wherein each of the plurality of secure digital communication devices and the server secure digital communication device comprises:
a streaming signal CODEC having a first interface and a second interface; and
a streaming signal transceiver having a first interface and a second interface,
wherein the secure digital communication device is installed in a workstation between an intranet and an internet over a firewall to form a physical isolation of the intranet and the internet, when a streaming signal CODEC of a first secure digital communication device of a first workstation receives a plurality of digital contents from the intranet through the first interface, the streaming signal CODEC of the first secure digital communication device encodes the plurality of digital contents received into a streaming signal, transmits the streaming signal through the second interface of the streaming signal CODEC to a first interface of a streaming signal transceiver of the first secure digital communication device, the streaming signal transceiver of the first secure digital communication device transmits the streaming signal through the second interface to a second interface of a streaming signal transceiver of a second secure digital communication device of a second workstation over the internet, and when the streaming signal transceiver of the second secure digital communication device receives the streaming signal through the second interface over the internet, the streaming signal transceiver of the second secure digital communication device transmits the streaming signal through the first interface of the streaming signal transceiver of the second secure digital communication device to the second interface of the streaming signal CODEC of the second secure digital communication device, the streaming signal CODEC of the second secure digital communication device decodes the streaming signal to the plurality of digital contents, and stores the plurality of digital contents decoded in the second workstation.

8. The secure digital communication system according to claim 7, wherein the plurality of digital contents comprises a word document, a spread sheet document, a power point presentation document, a PDF document, a text document, a still image, a video segment, and any combination thereof.

9. The secure digital communication system according to claim 7, wherein the streaming signal comprises an audio handshake signal, and a streaming media signal.

10. The secure digital communication system according to claim 9, wherein the audio handshake signal coordinates the transmission of the streaming media signal, and streaming media signal of the streaming signal comprises one or more QR codes, one or more color images, and one or more video segments.

11. The secure digital communication system according to claim 10, wherein an HDMI interface is installed between the second interface of the streaming signal CODEC and the first interface of the streaming signal transceiver of the secure digital communication device.

12. The secure digital communication system according to claim 11, wherein the streaming signal is transmitted over the HDMI interface, the audio handshake signal is transmitted through an audio channel of the HDMI interface; and the streaming media signal is transmitted through a display data channel of the HDMI interface.

13. A secure Picture Archiving and Communication System, comprising:
  a secure Picture Archiving and Communication System (PACS) server, wherein the secure PACS server is connected to a PACS database, and a server secure digital communication device;
  a plurality of PACS workstations installed in an intranet, wherein the plurality of PACS workstations connects to the secure PACS server over an internet; and
  a plurality of secure digital communication devices, wherein each of the plurality of secure digital communication devices connects to a corresponding PACS workstation to the server secure digital communication device of the secure PACS server to facilitate secure communication among the corresponding PACS workstation and the secure PACS server,
  wherein each of the plurality of secure digital communication devices and the server secure digital communication device comprises:
  a streaming signal CODEC having a first interface and a second interface; and
  a streaming signal transceiver having a first interface and a second interface,
  wherein the secure digital communication device is installed in a workstation between the intranet and the internet over a firewall to form a physical isolation of the intranet and the internet, when a streaming signal CODEC of a first secure digital communication device of a first PACS workstation receives a plurality of PACS contents from the intranet through the first interface, the streaming signal CODEC of the first secure digital communication device encodes the plurality of PACS contents into a streaming signal, transmits the streaming signal through the second interface of the streaming signal CODEC of the first secure digital communication device to a first interface of a streaming signal transceiver of the first secure digital communication device, the streaming signal transceiver of the first secure digital communication device transmits the streaming signal through the second interface to a second interface of a streaming signal transceiver of a second secure digital communication device of a second PACS workstation over the internet, and when the streaming signal transceiver of the second secure digital communication device receives the streaming signal through the second interface over the internet, the streaming signal transceiver of the second secure digital communication device transmits the streaming signal through the first interface to the second interface of the streaming signal CODEC of the second secure digital communication device, the streaming signal CODEC of the second secure digital communication device decodes the streaming signal to the plurality of PACS contents, and stores the plurality of PACS contents in the second PACS workstation.

14. The secure PACS according to claim 13, wherein the plurality of PACS contents comprises a word document, a spread sheet document, a power point presentation document, a PDF document, a text document, a still image, a video segment, and any combination thereof.

15. The secure PACS according to claim 13, wherein the streaming signal comprises an audio handshake signal, and a streaming media signal.

16. The secure PACS according to claim 15, wherein the audio handshake signal coordinates the transmission of the streaming media signal, and streaming media signal of the streaming signal comprises one or more QR codes, one or more color images, and one or more video segments.

17. The secure PACS according to claim 16, wherein an HDMI interface is installed between the second interface of the streaming signal CODEC and the first interface of the streaming signal transceiver of the secure digital communication device.

18. The secure PACS according to claim 17, wherein the streaming signal is transmitted over the HDMI interface, the audio handshake signal is transmitted through an audio channel of the HDMI interface; and the streaming media signal is transmitted through a display data channel of the HDMI interface.

* * * * *